United States Patent
Daft et al.

(10) Patent No.: US 9,274,088 B2
(45) Date of Patent: Mar. 1, 2016

(54) REDISTRIBUTION LAYER IN AN ULTRASOUND DIAGNOSTIC IMAGING TRANSDUCER

(75) Inventors: Christopher M. Daft, Dublin, CA (US); Paul A. Wagner, San Carlos, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 413 days.

(21) Appl. No.: 12/780,717

(22) Filed: May 14, 2010

(65) Prior Publication Data

US 2011/0021923 A1 Jan. 27, 2011

Related U.S. Application Data

(60) Provisional application No. 61/227,639, filed on Jul. 22, 2009.

(51) Int. Cl.

| | |
|---|---|
| *A61B 8/14* | (2006.01) |
| *G01N 29/06* | (2006.01) |
| *A61B 8/00* | (2006.01) |
| *G01N 29/24* | (2006.01) |
| *G01N 29/26* | (2006.01) |
| *G01S 7/52* | (2006.01) |
| *G01S 15/89* | (2006.01) |
| *A61B 8/08* | (2006.01) |

(52) U.S. Cl.
CPC .............. *G01N 29/0654* (2013.01); *A61B 8/54* (2013.01); *G01N 29/245* (2013.01); *G01N 29/262* (2013.01); *G01S 7/52085* (2013.01); *G01S 15/8925* (2013.01); *G01S 15/8927* (2013.01); *A61B 8/483* (2013.01)

(58) Field of Classification Search
None
See application file for complete search history.

(56) References Cited

U.S. PATENT DOCUMENTS

| | | | | |
|---|---|---|---|---|
| 5,902,241 | A * | 5/1999 | Seyed-Bolorforosh et al. | 600/443 |
| 5,931,785 | A * | 8/1999 | Mason | 600/459 |
| 6,676,602 | B1 * | 1/2004 | Barnes et al. | 600/443 |
| 6,836,159 | B2 * | 12/2004 | Wodnicki | 327/100 |
| 7,313,053 | B2 * | 12/2007 | Wodnicki | 367/153 |
| 7,353,056 | B2 * | 4/2008 | Hazard et al. | 600/407 |
| 2002/0135415 | A1 * | 9/2002 | Dufort | 327/333 |
| 2004/0122321 | A1 * | 6/2004 | Alexandru | 600/459 |
| 2005/0061085 | A1 * | 3/2005 | Jespersen | 73/861.27 |
| 2005/0148879 | A1 * | 7/2005 | Ramamurthy et al. | 600/459 |

(Continued)

OTHER PUBLICATIONS

Platt, John C., *Optimal Filtering for Patterned Displays*, IEEE Signal Processing Letters, vol. 7, No. 7, Jul. 2000, pp. 179-181.

*Primary Examiner* — James Kish
*Assistant Examiner* — Michael N Fisher

(57) ABSTRACT

Medical diagnostic ultrasound imaging is performed with a multi-dimensional transducer array and an imaging system for planar scanning. The elements of the array may be distributed on a periodic grid with aperiodic shifts in position. When a one-dimensional array is formed on the array, the aperiodic shifts better distribute acoustic energies, reducing peaks in side lobes. Using a layered structure of switches underneath the acoustic elements, side lobes may be further reduced. The switches are used for interconnecting elements to form macro elements of the one-dimensional aperture on the multi-dimensional array. The switches are distributed on a grid corresponding to the desired imaging frequency. The acoustic elements are distributed with a finer pitch. The finer pitch allows formation of the macro elements for the one-dimensional aperture where the edges of the macro elements have fewer or no periodic patterns.

21 Claims, 11 Drawing Sheets

(56) References Cited

U.S. PATENT DOCUMENTS

2005/0267369 A1* 12/2005 Lazenby et al. .............. 600/447
2007/0016026 A1* 1/2007 Thomenius et al. .......... 600/437
2009/0082673 A1* 3/2009 Lu et al. ........................ 600/459

* cited by examiner

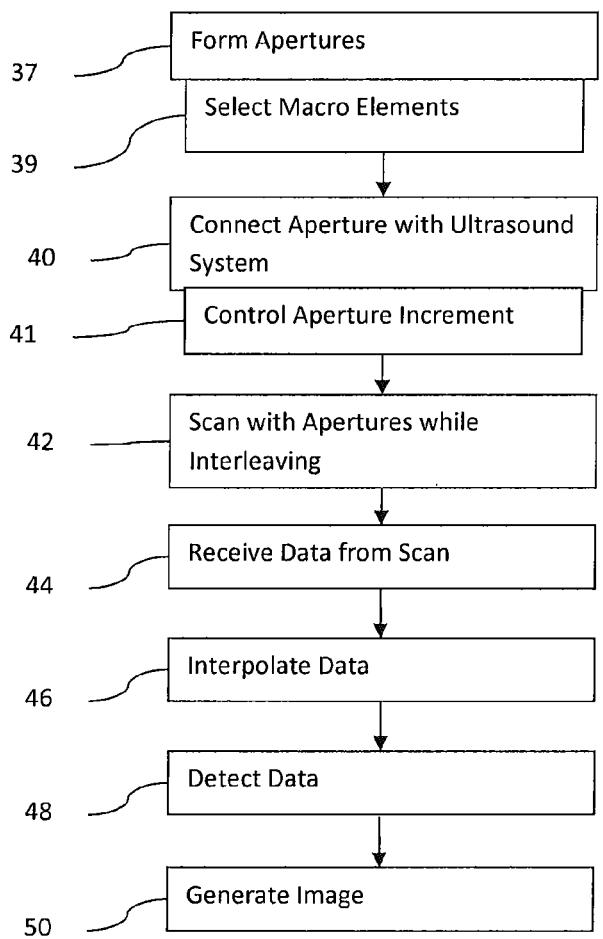
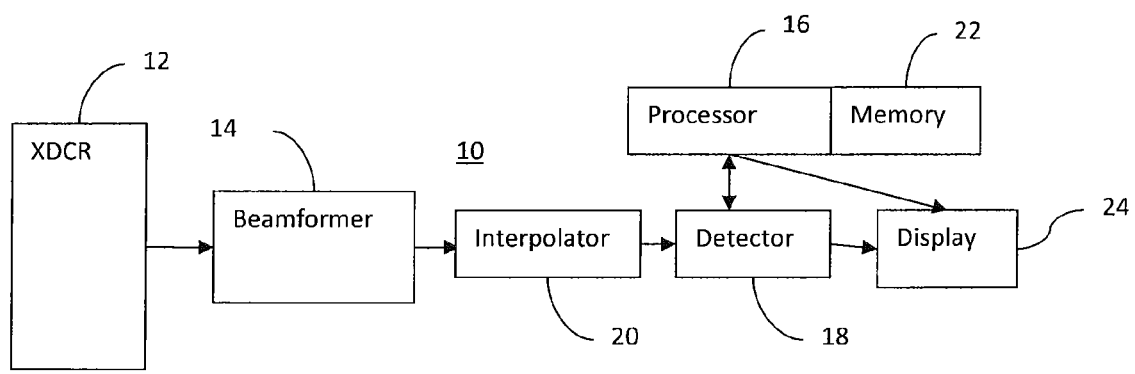

REDISTRIBUTION LAYER IN AN ULTRASOUND DIAGNOSTIC IMAGING TRANSDUCER

RELATED APPLICATIONS

The present patent document claims the benefit of the filing date under 35 U.S.C. §119(e) of Provisional U.S. Patent Application Ser. No. 61/227,639, filed Jul. 22, 2009, which is hereby incorporated by reference.

BACKGROUND

The present embodiments relate to ultrasound transducers. In particular, the present embodiments relate to a reconfigurable transducer array.

One-dimensional transducers are used to scan a plane with electronic steering. For scanning a volume, a two-dimensional transducer may be used. However, the number of beamforming channels greatly increases for scanning with a two-dimensional transducer. Many ultrasound imaging systems do not have sufficient channels. An alternative is a mechanically rotated one-dimensional transducer (i.e., a wobbler). However, the mechanical motion may be insufficiently rapid for real-time volume scanning.

A multi-dimensional transducer array may be used with electronic switching to both provide for volume scanning and a fewer number of required beamformer channels. U.S. Pat. No. 6,676,602 describes such embodiments. For example, an electronically rotated array is an array of elements where the aperture used during scanning is electronically controlled. Switches connect different elements to different beamformer channels, allowing rotation of the aperture for sequential scanning. For example, a one-dimensional aperture is rotated electronically on the face of a two-dimensional transducer array. By controlling the configuration of the switches, the one-dimensional array may be oriented to any rotational angle. Within a given aperture, the defined one-dimensional array may steer scan lines. For volume scanning, the volume is sampled by collecting a series of azimuth-spaced beam groups at each rotation angle.

The switching to allow beamformation in real-time volume scanning may require high performance switches. From an electronic perspective, an aperture comprised of an ordered or periodic cell structure is desirable because the periodic cell structure allows macro elements to be wired up to edge traces using the fewest number of in-series switches, relaxing the "on" resistance (Ron) requirements for the switches.

Fitting a one-dimensional aperture on a multi-dimensional array may result in imaging artifacts. Beamforming problems can arise from "pixelation" errors incurred while mapping an angled 1D array onto a periodic 2D grid. Jogs in the elements concentrate energy into localized field side lobes that degrade contrast resolution.

BRIEF SUMMARY

The present invention is defined by the following claims, and nothing in this section should be taken as a limitation on those claims. By way of introduction, the preferred embodiments described below include methods and systems for medical diagnostic ultrasound imaging with a multi-dimensional transducer array. The elements of the array may be distributed on a periodic grid with aperiodic shifts in position. When a one-dimensional array is formed on the array, the aperiodic shifts better distribute acoustic energies, reducing peaks in side lobes. Using a layered structure of switches underneath the acoustic elements, side lobes may be further reduced. The switches are used for interconnecting elements to form macro elements of the one-dimensional aperture on the multi-dimensional array. The switches are distributed on a grid corresponding to the desired imaging frequency. The acoustic elements are distributed with a finer pitch. The finer pitch allows formation of the macro elements for the one-dimensional aperture where the edges of the macro elements have fewer or no periodic patterns, resulting in reduced side lobes. The difference in pitch may be used for other purposes.

In a first aspect, a multi-dimensional transducer is provided for medical diagnostic ultrasound imaging. A switching layer has a plurality of switch cells. Each cell includes at least one lateral switch for connecting to an adjacent cell and at least one vertical switch for connecting to an acoustic element. An acoustic element layer has a plurality of acoustic elements. The acoustic element layer is stacked along a depth dimension with the switching layer. The acoustic elements of the acoustic element layer have a finer pitch than the switch cells of the switch layer.

In a second aspect, a method is provided for operating a two-dimensional transducer array in medical diagnostic ultrasound imaging. A plurality of different one-dimensional apertures is defined on a multidimensional array of transducers. Each of the different one-dimensional apertures corresponds to a different aperture rotation angle relative to the multidimensional array. Substantially parallel groups of the transducers are selected for elements of the one-dimensional apertures. The selected transducers in the groups are aperiodic along an elevation length of the corresponding elements.

In a third aspect, a multi-dimensional transducer is provided for medical diagnostic ultrasound imaging. A plurality of transducer elements is provided. A plurality of switches is configured to connect the transducer elements into a one-dimensional array of macro elements. The macro elements are formed from groups of the transducer elements grouped such that different macro elements have edges with variation away from straight at different distances along an elevation length than others of the macro elements. The variation is irregular for the macro elements.

Any one or combinations of any two or more of the aspects discussed above may be used. Further aspects and advantages of the invention are discussed below in conjunction with the preferred embodiments.

BRIEF DESCRIPTION OF SEVERAL VIEWS OF THE DRAWINGS

The components and the figures are not necessarily to scale, emphasis instead being placed upon illustrating the principles of the invention. Moreover, in the figures, like reference numerals designate corresponding parts throughout the different views.

FIG. 1 is a block diagram of one embodiment of a system for scanning with ultrasound;

FIG. 10 is a flow chart diagram of one embodiment of a method for scanning with ultrasound;

DETAILED DESCRIPTION OF THE PREFERRED EMBODIMENTS

Figure 2:
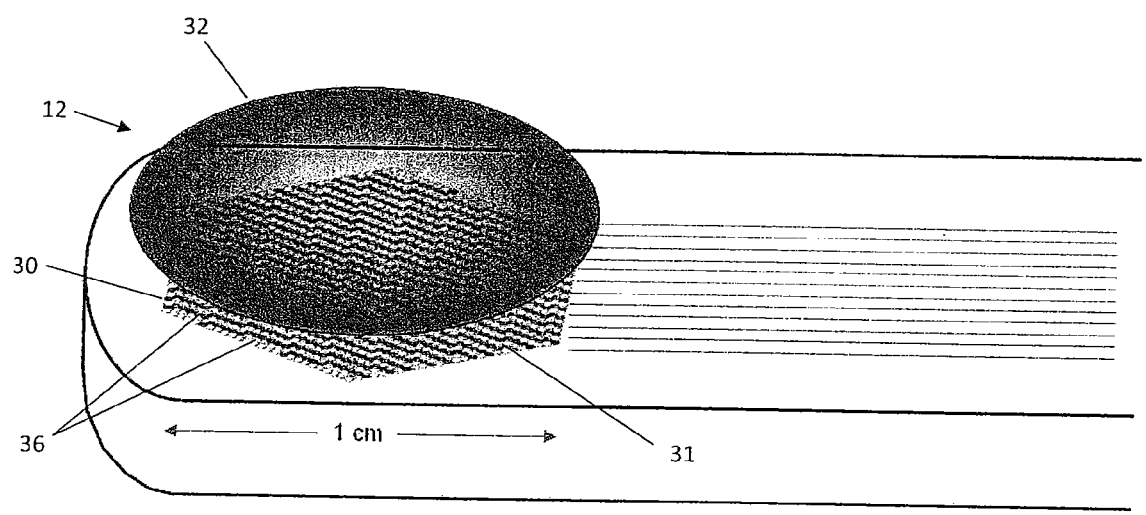
FIG. 2 is a graphical illustration of a probe having a multi-dimensional array according to one embodiment.

Electronically rotatable one-dimensional ultrasound arrays may provide a simplified and low cost real-time three-dimensional volume acquisition suitable for cardiac or other imaging. Fewer beamforming channels may be needed than scanning with a fully sampled two-dimensional array.

A randomized or aperiodic cell structure provides better beam quality than a periodic structure. An acoustic cell pitch less than or equal to half the macro element width may allow for aperiodic macro elements in addition to or alternative to aperiodic cell structure alone. In one embodiment, a coarse periodic electronic cell grid is combined with a finer aperiodic acoustic cell grid for increasing imaging performance.

In one embodiment, a reconfigurable array architecture has an electronic cell matrix interconnected laterally by a first set of switches and an overlaid acoustic cell matrix connected "vertically" to nearby electronic cells by a second set of switches. The electronic cell matrix may have hexagonal, rectangular, or triangular periodicity, and the acoustic cell matrix may have an intentionally different periodicity or is aperiodic. For example, with hexagonal electronic cell periodicity, three lateral switches per electronic cell, a variable number (e.g., 7—one element and each surrounding element) of vertical switches per cell, and aperiodic acoustic cell distribution are provided. The lateral set of switches is optimized to have a low On-resistance, and the vertical set of switches is optimized to have a higher On-resistance. Higher On-resistance may reduce the amount of silicon real estate used by the switches. A set of entry switches may be placed along geometric diagonals or sub-diagonals, and a layer of radio frequency (RF) traces route these entry switches out to one or more edges of the array.

FIG. 1 shows a system 10 for scanning with a multi-dimensional transducer for medical diagnostic ultrasound imaging. The system 10 includes a transducer probe 12, a beamformer 14, a processor 16, a detector 18, an interpolator 20, a memory 22, and a display 24. Additional, different, or fewer components may be provided. For example, the system 10 includes a user interface. In one embodiment, the system 10 is a medical diagnostic ultrasound imaging system. In other embodiments, the processor 16 and/or memory 22 are part of a workstation or computer different or separate from an ultrasound imaging system. The workstation is adjacent to or remote from the ultrasound imaging system.

The transducer probe 12 may be used with the system of FIG. 1 or a different system. The transducer probe 12 is a planar array, a curved array, a two-dimensional array, a radial array, an annular array, or other multidimensional array of transducer elements. For example, the transducer probe 12 is a multi- or two-dimensional array. In one embodiment, the transducer probe 12 is adapted for use external to the patient, such as including a hand held housing or a housing for mounting to an external structure. As another example, the transducer probe 12 is adapted for use within the patient, such as a transesophegeal probe, an endocavity probe or other probe for scanning while positioned within or in the interior of a patient. For example, the transducer is used as an electrically rotatable 1D transesophegeal (TEE) probe as represented by FIG. 2. A 1 cm hex array with about 2000 elements is provided, where the array is used with about 48 beamformer channels and associated coaxial cables and a bias line (in the case of a capacitive transducer or cMUT). Other sizes, numbers of elements, and/or numbers of channels may be provided.

Electronic rotation may be performed at a higher speed than mechanical rotation. For example, the one-dimensional array aperture may be electronically rotated to any angle in micro or nano seconds, enabling real-time volumetric imaging while minimizing cable count between the system and the transducer.

The multi-dimensional transducer probe 12 is an array of an N by M arrangement of acoustic elements, where N and M are both greater than one. The area array sampling pattern or relative placement of one acoustic element to another acoustic element is based on any sampling method, such as a triangular grid, rectangular grid, hexagonal grid, irregular grid, or random grid. Various spacing may be provided, such as ½ or one wavelength spacing between the centers of adjacent elements. In one embodiment, the grid has about ⅓ or ¼ wavelength spacing. The face or surface of the entire array is square, rectangular, triangular, hexagonal, irregular, or other shape. Any of various possible multi-dimensional arrangements of acoustic elements may be used for the multi-dimensional transducer probe 12. The array 31 is either flat or includes concave or convex curvature.

An electronically rotated phased array may be implemented using the multi-dimensional array 31 of acoustic elements 36 and an array of semiconductor or MEMS switches. The switches electronically connect elements into a phased array of elements 38. The elements 38 are individual elements 36 of the array 31 or are formed by interconnection of a plurality of elements 36 to form macro elements 38. For focal point locations over most of the depth of the beam, the macro elements 38 may be a plurality of parallel, substantially straight lines. Where response time of switches within the electronically configurable array is sufficient, the interconnection of acoustic elements 36 to correspond with constant delay contours dynamically changes during the reception of a beam, such as changing from concentric circular, to elliptical, and to substantially straight macro elements 38. Also, the macro elements 38 may represent a contour derived from and used for multiple focal points without any dynamic changes for a given beam or scan plane. Alternatively or additionally, the macro elements 38 are grouped, such as in rows, corresponding to different focal points. Different rows or all of the rows are used for different focal points. The macro elements 38 are aligned in an image plane direction. By reconfiguring the macro elements 38, the image plane direction is rotated for scanning the three-dimensional volume. A set of rotated two-dimensional image planes are acquired as a three-dimensional data set. The rotated phased array of macro elements 38 may be either a 1D, 1.75D or other phased array. In alternative embodiments, macro elements 38 are not used. Instead, a 1D, 1.75D or other array is formed from elements of the multi-dimensional transducer without combining elements into macro elements 38.

The transducer probe 12 includes an acoustic element layer 30, a lens 32, and a switch layer 34. Additional, different or fewer components may be provided. For example and as shown in FIG. 2, a housing may be provided.

The acoustic element layer 30 is planar, curved, concave, convex or other surface shape. The acoustic element layer 30 includes a plurality of acoustic elements 36. The acoustic element layer 30 is a single layer of acoustic elements 36 or may include multiple layers of acoustic elements 36. The acoustic elements 36 are transducer elements for transducing between electrical and acoustic energies.

The acoustic elements 36 of the transducer probe 12 are lead zirconate titanate (PZT) piezoelectric transduction material, ferroelectric relaxor or PVDF materials, capacitive membrane ultrasonic transducer (cMUT) materials, micro-machined membranes or beams, microelectromechanical devices, other piezoelectric material, or other means for acoustic-to-electric and/or electric-to-acoustic transduction. For example, the acoustic elements 36 are cMUT or micromachined structures, such as at least one flexible membrane suspended over a gap with electrodes on each side of the gap for transducing between acoustic and electrical energies. Each acoustic element 36 is formed from one or more, such as 4-8, tens or other numbers of membranes and gaps (i.e., "drums" or cMUT cells). The electrodes of each of the membranes and gaps for a given element 36 are connected in common to form the single acoustic element 36.

All of the acoustic elements 36 comprise a same type of material, but multiple types of acoustic transducer materials may be used for different acoustic elements 36. The acoustic elements 36 have one of various possible shapes, such as triangular, rectangular, square, polygonal, hexagonal, circular, irregular, or any combination of shapes on the face of the acoustic element 36 (i.e., portion of the element 36 placed adjacent a volume to be scanned).

The transducer probe 12 converts between electrical signals and acoustic energy for scanning a region of the patient body. The region of the body scanned is a function of the type of transducer array 31, position of the transducer probe 12 relative to the patient, and the underlying switch setting. At a given switch configuration, a linear aperture may scan a rectangular or square, planar region of the body. As another example, a curved linear aperture may scan a pie shaped region of the body. Scans conforming to other geometrical regions or shapes within the body may be used, such as Vector® scans. The scans are of a two-dimensional plane. Different planes or different segments of a plane may be scanned by moving an aperture of the transducer probe 12. The aperture may be electronically moved without movement of the transducer probe 12. A volume is scanned. The volume is scanned by electronic steering and switching.

Figure 3:
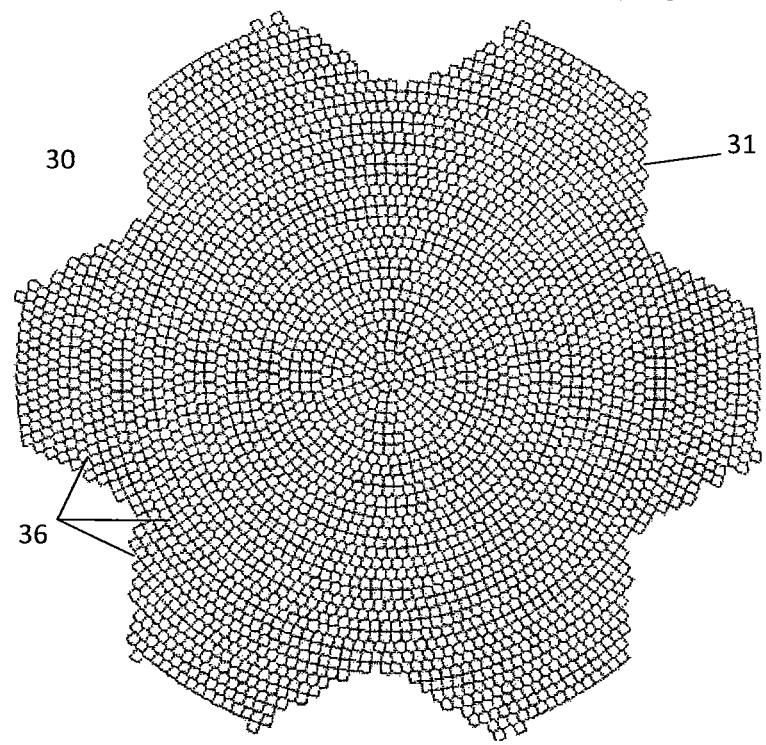
FIG. 3 is a top view of one embodiment of a distribution of acoustic elements in multi-dimensional array.

In one embodiment, the acoustic elements 36 are aperiodic across a face of the transducer array 31. FIG. 3 shows aperiodic distribution of the acoustic elements 36 in a radially symmetric pattern. Radial symmetry may not be provided in other embodiments. The acoustic elements 36 are generally positioned in a periodic or regular grid. One or more of the elements, such as a majority or all of the elements are shifted in different directions and/or by different amounts to create an aperiodic pattern. The shifts are by less than a pitch of the grid, such as being 10-100 microns where each acoustic element is about 0.2 mm in diameter. "About" accounts for manufacturing tolerance or other differences within 10%. Other sizes of elements 36 and/or shifts could be used. The aperiodic arrangement of the acoustic elements 36 leaves gaps between the elements. Alternatively, the elements are sized differently to account of the shifts. Aperiodic shifts may be provided by a partially randomized radial layout format or other shift distribution.

Where the acoustic elements 36 are cMUTs, the array 30 is formed using lithography or other semiconductor process. The pattern of the acoustic elements 36, such as the aperiodic pattern, is designed and used for forming the array 31.

In alternative embodiments, the acoustic elements 36 are patterned periodically or on the base periodic grid. The acoustic elements 36 may have a same or different periodicity as the switches of the switch layer. For example, periodic distribution of the acoustic elements 36 is provided, but with a different pitch than of the switches used for forming the apertures.

The acoustic layer 30 is stacked along a depth dimension or generally orthogonally to the face of the acoustic layer 30 with the switch layer 34. "Generally" accounts for curvature of the acoustic layer 30 and/or the switch layer 34 or manufacturing tolerance. In one embodiment, the stacking is conceptual as the layers are formed in the same silicon substrate. In other embodiments, the layers 30, 34 are formed on different structures and are literally stacked. None, one or more other layers of material or structure may be positioned in between the acoustic element layer 30 and the switch layer 34.

Figure 4:
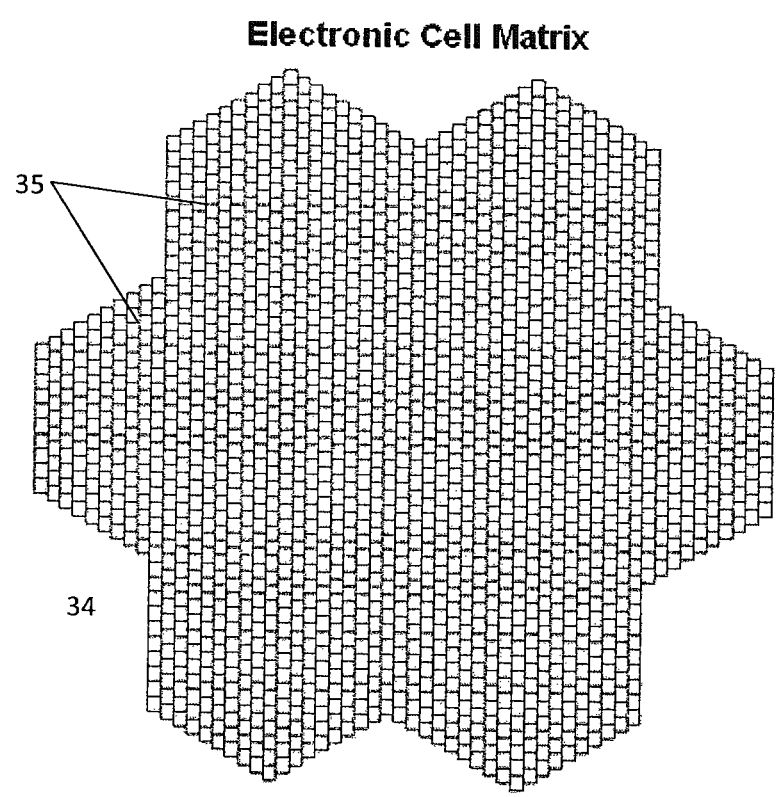
FIG. 4 is a top view of one embodiment of a distribution of switch cells in multi-dimensional array.

FIG. 4 shows the switch layer 34. The switch layer 34 is planar, curved, concave, convex or other surface shape. The switch layer 34 includes a plurality of switches. The switch layer 34 is a single layer of switches or may include multiple layers of switches. The switches are for connecting beamformer channels with acoustic elements 36 and interconnecting acoustic elements 36.

The switches for forming the electronically rotating aperture are semiconductor switches, transistors, MEMS switches or other switches for electrically connecting or disconnecting elements and/or system channels of the beamformer 14 (see FIG. 1). In one embodiment, different MOSFETs are used, such as high voltage MOSFETS with control transistors. In another embodiment, the switches are bi-directional high-voltage switches with two pass MOSFETs, and a control for the MOSFETs where the gates float during imaging. The switches are sized so that the switch layer 34 covers the area of the acoustic layer 30 without being substantially larger or smaller, but other sizes may be provided. "Substantially" accounts for manufacturing tolerance, extra area associated with entry switches, or a few wavelengths. The switches are fabricated using semiconductor fabrication processes allowing a large number of devices to be fabricated on a single silicon or other semiconductor chip, but two or more chips may also be used. It is possible to include electronic circuitry and switches on the same silicon chip, allowing the switch control circuitry to be integrated with the switches on the same chip. The switches and array may be provided in a probe housing, providing a small, low cost, high yield three-dimensional imaging transducer using low power consumption, resulting in better transducer thermal efficiency. Minimal or no changes are needed in conventional imaging system channel hardware.

Figure 6:
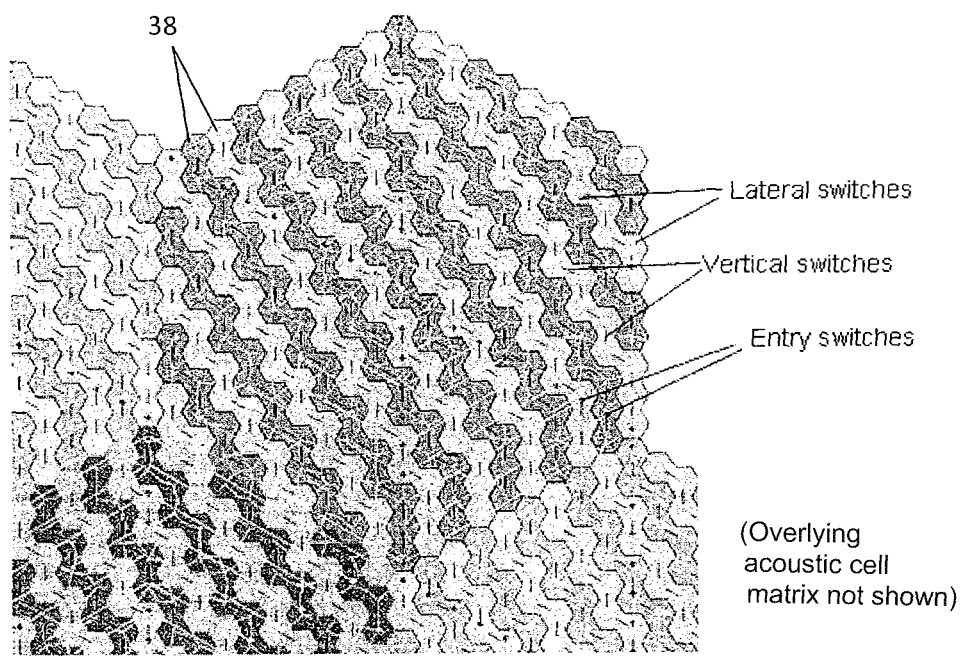
FIG. 6 is a top view of part of an acoustic element distribution with switches forming macro elements in one embodiment.

The switches are operable to interconnect the acoustic elements 36 into a plurality of macro elements 38 (see FIG. 6). Each macro element 38 includes at least two electrically connected acoustic elements 36. For example, the acoustic elements 36 are connected in a substantially straight line, chevron patterns or in curving patterns in at least two dimensions (i.e. across the face of the transducer array 31). For operation as a phased array, each macro element 38 is continuous across the face of the two-dimensional array 31 or a defined aperture.

The switches are high voltage (e.g., tens or hundreds of volts), small footprint switches. The switches may be integrated directly under the acoustic elements 36 to minimize interconnect parasitic capacitance.

The switches may be formed into switch cells 35. The switch cells 35 are distributed in the switch layer 34 in a regular hexagonal, rectangular, triangular, or other grid. The distribution is periodic, but may be randomized or aperiodic. The distribution is the same or different grid pattern, lateral extent, and number as the acoustic elements 36 of the acoustic layer 30.

Each switch cell 35 includes a plurality switches. For example, one or more lateral switches are provided for connecting to adjacent switch cells 35. In a hexagonal grid, three lateral switches may be provided in each switch cell 35 for connecting with three of the six adjacent switch cells 35. By arranging the lateral switches in each switch cell 35, different interconnections between a given switch cell 35 and the six adjacent switch cells 35 may be provided.

Each switch cell 35 includes one or more (e.g., at least two) vertical switches for connecting the switch cell 35 to a respective one or more acoustic elements 36. Vertical and lateral are used to describe the connection rather than the layout or orientation of the switch. Any layout or orientation may be used, such as the lateral switches surrounded by vertical switches, all formed in a same plane. In one embodiment, six or seven vertical switches are provided in each switch cell 35. Each vertical switch connects to one of six or seven adjacent acoustic elements 36. The adjacent acoustic elements 36 are adjacent to each other. A given acoustic element 36 may connect to one or more switch cells 35, but the switches are operated to avoid connection of different switch cells 35 to a same acoustic element 36 at a same time unless sharing a same beamformer channel.

A sub-set of the switch cells 35 include entry switches. The entry switches connect the beamformer channels with macro elements 38. In one embodiment, the entry switches are in switch cells 35 arranged along a geometric diagonal (primary) or three straight lines of the hexagonal grid. Other arrangements of entry switches may be provided.

Figure 5:
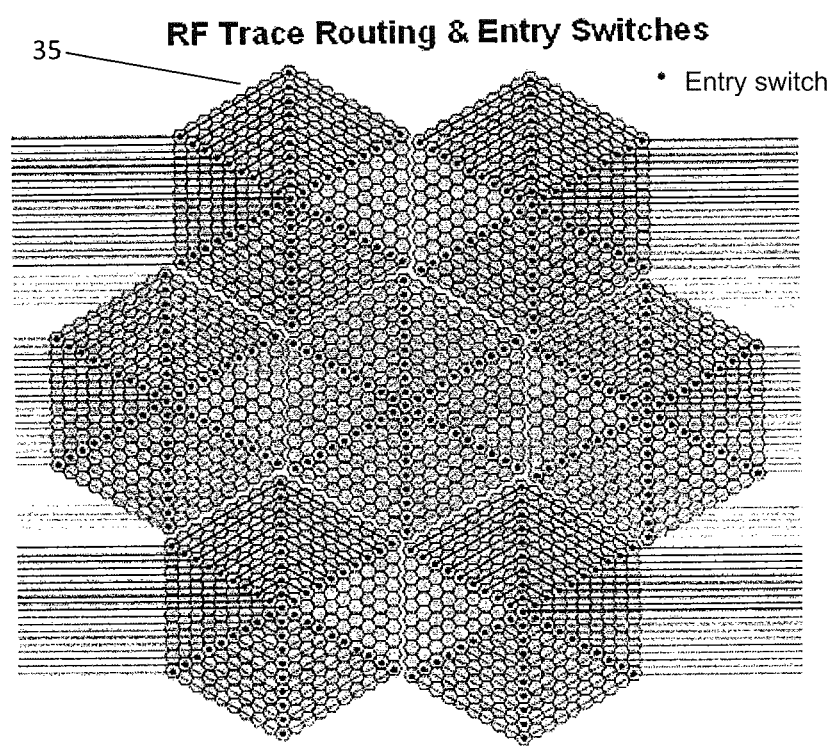
FIG. 5 is a top view of example channel connectability of the switch cells of FIG. 4.

FIG. 5 shows one embodiment of the switch layer 34. The switch layer 34 includes seven hexagonal regions with hexagonally distributed switch cells 35 in each of the hexagonal regions. Other numbers of regions (e.g., only one) or layout patterns (e.g., hexagonal cell distribution in a generally square or circular array) may be used.

The switch layer 34 provides for routing one-dimensional array signals into and out of the two-dimensional switch cell matrix. Entry switches are shown as dots in the center of some of the switch cells 35. The traces from the beamformer channels or coaxial cables connect or are connectable with three different entry switches as shown, but may connect with more or fewer. In the embodiment of FIG. 5, seven regions are each operated by 49 signal lines (48 beamformer channels and one bias line) for a total of 343 signal lines for about 14,000 switch cells 35. Other numbers may be used.

FIG. 6 shows a blow up of the switch layer 34 of FIG. 5. In FIG. 6, the macro elements 38 are formed by interconnecting lateral switches. One of the entry switches connects with each of the macro elements 38. The entry switches used to connect the macro elements 38 at the configured angle are shown as white and the unused or disconnected entry switches are shown as black. The lateral switches interconnect the switch cells 35 for the macro elements 38. The vertical switches for each switch cell 35 connect one or more acoustic elements 36 (not shown in FIG. 6) to the switch cell 35, completing the interconnection of the beamformer channel with the acoustic elements 36 in macro elements 38 for an aperture operating as a one-dimensional array. The other regions of the switch layer 34 operate in a similar manner to form the one-dimensional aperture.

Other layouts of switch cells 35, grids, and interconnections are possible. For example, the switch cells 35 operate differently to form the macro elements 38 at different angles. The same or different entry switches are used depending on the angle of the macro elements 38. By using regions on the switch layer 34, the number of acoustic elements 36 and/or switch cells 35 used for a given macro element 38 may be limited, such as to fewer than ten (e.g., nine) or other number of serially connected high voltage lateral switches. By limiting the number of switches, the resistance requirements for the switches may be reduced, resulting in smaller sized switches. Greater numbers of switches may be used for a given macro element 38.

The lateral, entry, and vertical switches are the same or different. In one embodiment, the entry switches are the same as the lateral switches, but both are different than the vertical switches. The vertical switches are designed to have a higher "on" resistance (Ron) than the lateral switches. Low Ron switches occupy a larger area. The low Ron lateral switches feed current into the macro element chain, while high Ron, smaller area "vertical" switches redistribute reduced amounts of current from the electronic cell matrix to the acoustic cell matrix 2D elements. The vertical switches may have higher Ron, to reduce the area. In one embodiment, all of the vertical switches have the same Ron characteristic within manufacturing tolerance. In other embodiments, one or more of the vertical switches may have even higher Ron than other vertical switches. For example, primary switch cell to acoustic element connections have a lower Ron vertical switch. Secondary vertical switches connect with secondary acoustic elements (e.g., adjacent). The higher Ron routes less of the electrical energy to that element, causing contribution but to a lesser extent in beamformation. By planning the distribution of primary and secondary vertical switches, such as one acoustic element 36 being connected through a primary vertical switch to one switch cell 35 and being connected to an adjacent switch cell 35 through a secondary vertical switch, most or all of the acoustic elements 36 may be used as "full strength" elements or "lesser" strength elements.

Referring again to FIG. 2, the spherical lens 32 is stacked above the switch layer 34 and the acoustic layer 30. In other embodiments, a lens with no focus, no lens, or another lens is provided. The lens 32 is an acoustic window. The spherical lens 32 assists with beam formation in concert with electronic rotation of a one-dimensional array since the spherical lens always focuses the sound in the direction perpendicular to the rotated row of elements, regardless of the rotation angle. The lens 32 provides elevation focus at a desired depth regardless of the angle of rotation of the one-dimensional aperture on the array 31.

Figure 7:
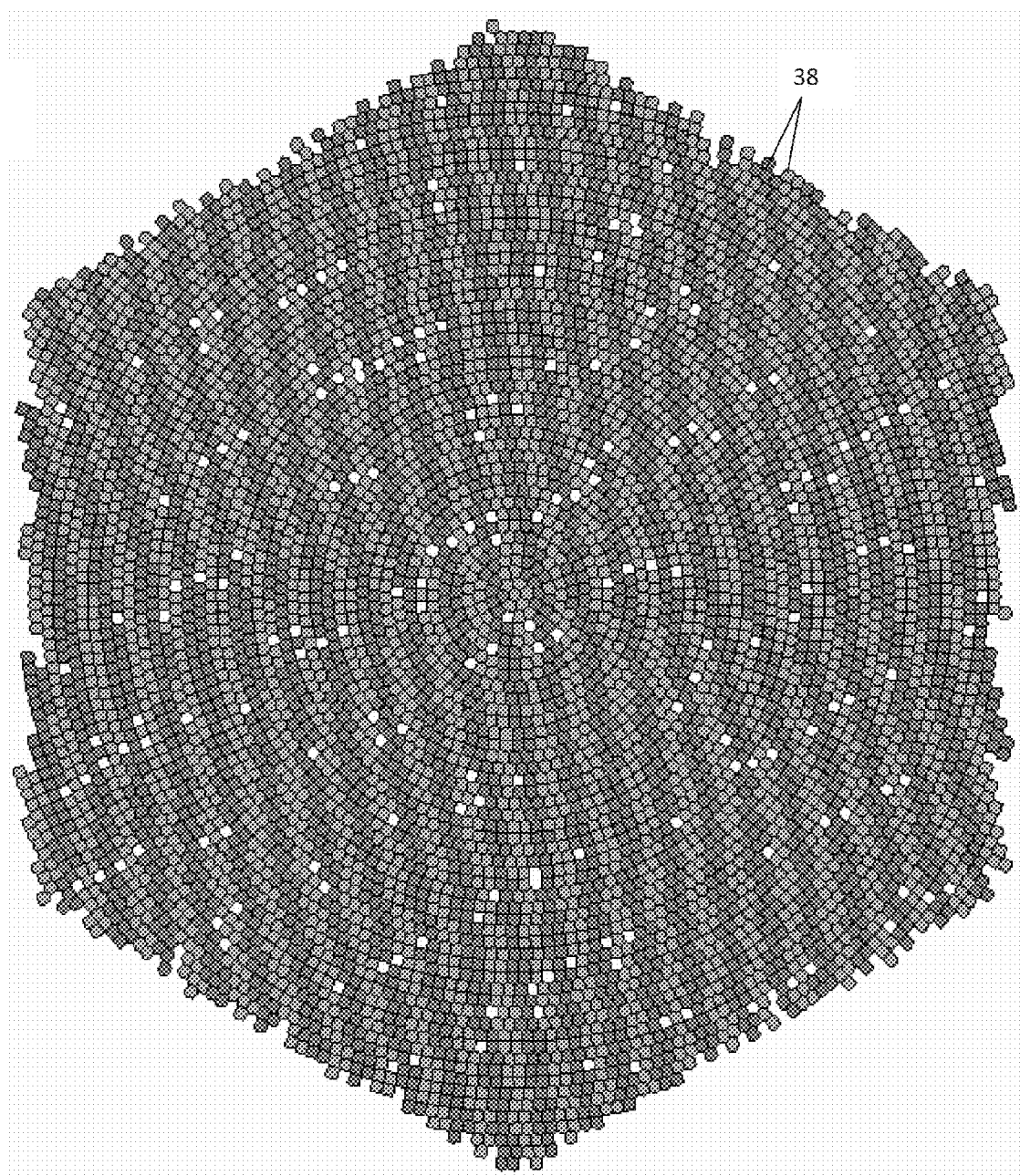
FIG. 7 is a top view of one embodiment of the distribution of acoustic elements of FIG. 3 with interconnected elements forming macro elements in a one-dimensional array and with irregular edges.
Figure 8:
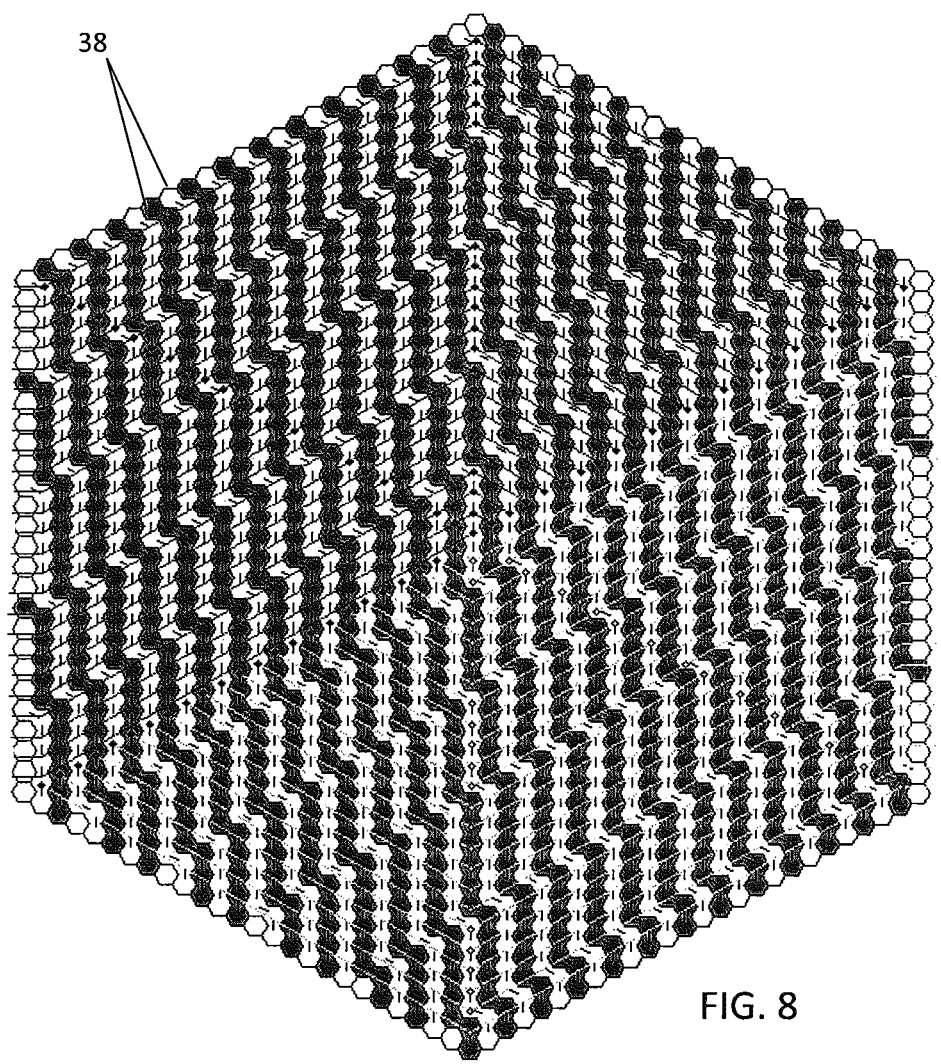
FIG. 8 is a top view of one embodiment of a distribution of acoustic elements in a regular or periodic grid with interconnected elements forming macro elements in a one-dimensional array and with periodic edges.

As shown in FIGS. 6, 7, and 8, the switch layer 34 is configured to form macro elements 38. In one embodiment, the configuration (e.g., selection of which switches are open and which are closed) is stored in a memory in the transducer probe 12. The memory may be programmable or read only. The memory stores different configurations, each associated with a different one-dimensional aperture. For example, different configurations are provided for different angles of rotation, translations and/or depths of focus of the one-dimensional aperture. FIG. 6 shows a different angle than FIGS. 7 and 8 for the macro elements 38 and the corresponding one-dimensional aperture. The different configurations may be indexed by rotation angle or merely a next increment command. In other embodiments, the switch configuration is programmed, set, or controlled by the imaging system with or without a memory in the transducer probe 12.

The one-dimensional aperture is a one-dimensional array of one-dimensional array elements (i.e., macro elements 38). Due to the layout or connectability of the switches of the switch layer 34, the switches are configured to form the acoustic elements 36 into the one-dimensional array of macro elements 38. The acoustic elements 36 are connected together so that the same beamformer channel connects with the acoustic elements 36 of the same macro element 38. When connected, the switches are configured in the one-dimensional aperture.

The one-dimensional aperture of macro elements 38 may be used to scan a plane. Transmit and receive beams may be steered to various angles, such as +/−45 degrees (theta) with time delay focusing of the beamformer 14. Combined with rotation (phi) of the aperture, acoustic transmit and receive beam may be focused anywhere within the 90 degree cone extending out from the face of the acoustic layer 30. In the embodiment shown in FIG. 2, the 2000 element 2D acoustic layer 30 or matrix may be electronically configured into about 50 macro elements 38 as a 1D transducer or aperture with elements oriented at any rotational angle (phi). By resetting the switches, additional one-dimensional arrays are formed rotated relative to each other on the acoustic element layer 30. Each rotation is associated with at least one switch being set differently. For some rotations, the switches may be associated with the same or different connections of the lateral, vertical, and entry switches.

In one embodiment, the acoustic elements 36 of the acoustic layer 30 have a finer pitch than the switch cells 35 of the switch layer 34. This is in addition to or as an alternative to the aperiodic distribution of acoustic elements 36 in the acoustic layer 30. The difference in pitch between the switch cells 35 and the acoustic elements 36 is from a different general, average, or overall periodicity (i.e., different size grid). In one embodiment, the switch cells 35 have a more coarse $\lambda/2$ pitch to maximize the silicon area available to place high voltage switches. The corresponding grid (e.g., hexagonal, rectangular, or triangular periodicity grid) may maximize signal routing efficiency. The acoustic elements 36 have a finer pitch, such as $\lambda/2$ or less (e.g., $\lambda/3$, $\lambda/4$, or other). Since each switch cell 35 is connectable with a plurality of acoustic elements 36, the difference in pitch still provides for selection of most, if not all, of the acoustic elements 36 (see FIG. 7 where white acoustic elements 36 are not connectable with switch cells 35 due to shifting and/or difference in periodicity). In other embodiments, the pitch is the same or the acoustic elements 36 have a more coarse pitch than the switch cells 35.

FIG. 8 shows macro elements 38 with regular variation formed on a hexagonal grid system. Every sixth acoustic element 36 along a length of each macro element 38 (e.g., along the elevation length of the macro element 38) is associated with a jog or step. Different macro elements 38 may have the same or different periodicity. The periodicity may be more complex, such as being a combination of two frequencies (e.g., every fifth and every eighth steps). The macro elements 38 of FIG. 8 may be formed by switch cells 35 with a same periodicity as acoustic elements 36.

The difference in pitch allows formation of macro elements 38 having irregular variation. FIG. 7 shows macro elements 38 formed with the switch layer 34 having a different pitch than the acoustic layer 30. In FIG. 7, the acoustic elements 36 also have randomized or partially randomized shifts. In other embodiments, the acoustic elements 36 do not have the randomized shifts. The difference in pitch allows for further randomization or otherwise more aperiodic macro elements 38.

The irregular variation is of the acoustic elements 36 in a given macro element 38, the edges of the macro element 38, and/or the steps of the macro element 38. By partially randomizing the acoustic elements 36 selected to be in a macro element 38, the periodic steps along the edge of the macro element 38 may be removed or reduced. The steps are performed in smaller increments and/or at different distances along the elevation length. For a given macro element 38, the steps are aperiodic or less periodic than for FIG. 8. Alternatively or additionally, the steps or periodicity across macro elements is different. The steps for a given macro element 38 occur at different distances along the elevation length and/or with a different periodicity than for adjacent macro elements 38.

This irregular pattern in the macro elements 38 is along the angle desired for the macro element 38. A straight line defines the desire macro element 38. The acoustic elements 36 contacting the straight line are connected, but a one or more may not be. Acoustic elements 36 adjacent to the straight line are either included in the macro element 38, an adjacent macro element 38, or no macro element 38. By randomizing or selecting to have less periodic steps, these adjacent acoustic elements 36 are assigned to macro elements 38. The result may be the macro element 38 having different azimuth width at different locations along the elevation length, but the differences in width are aperiodic, partially randomized, or have a higher frequency of periodicity than as shown in FIG. 8.

Figure 9A:
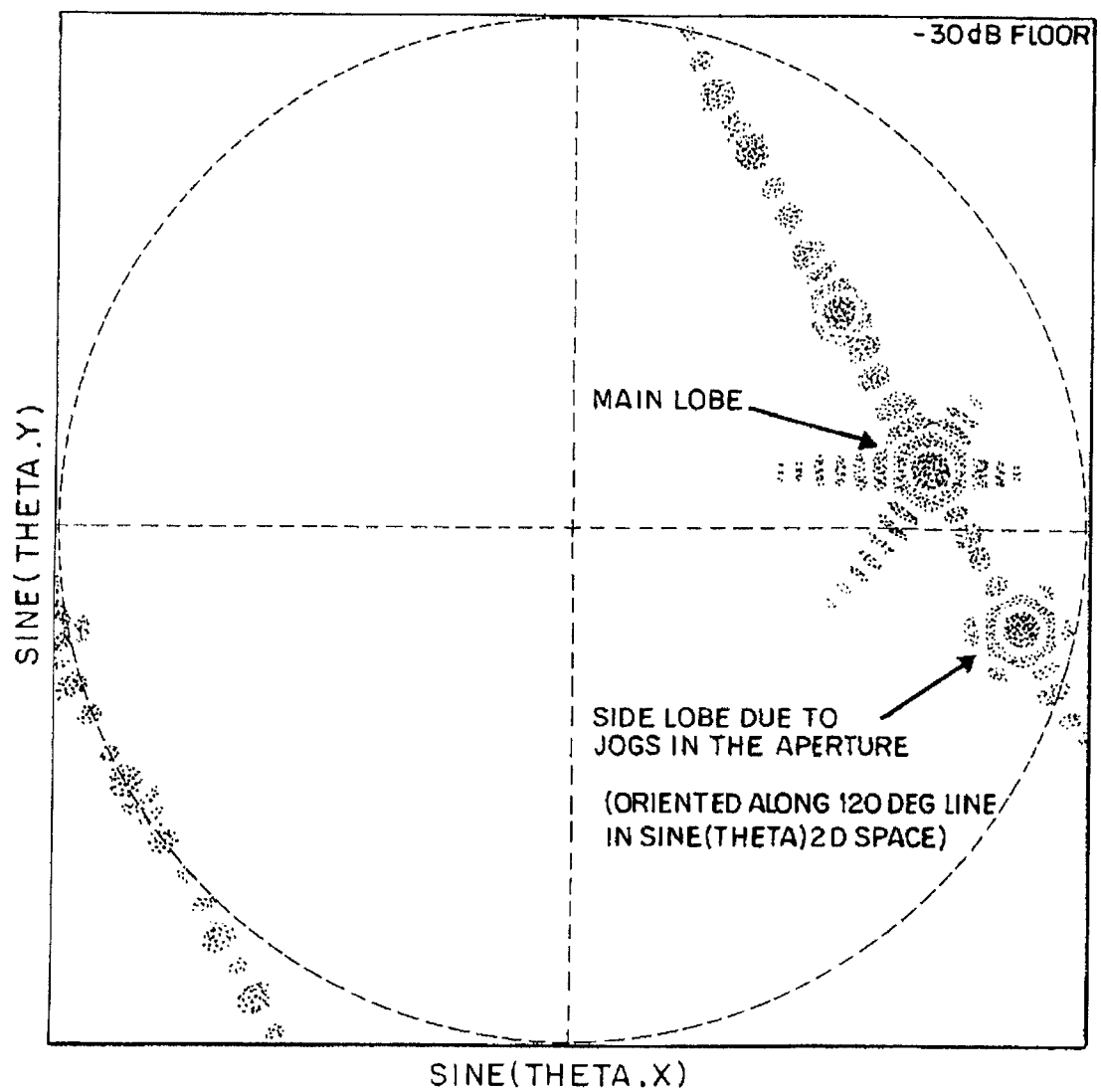
FIGS. 9A and 9B are beam plots showing side lobe levels associated with scanning using the apertures of FIGS. 8 and 7, respectively.
Figure 9B:
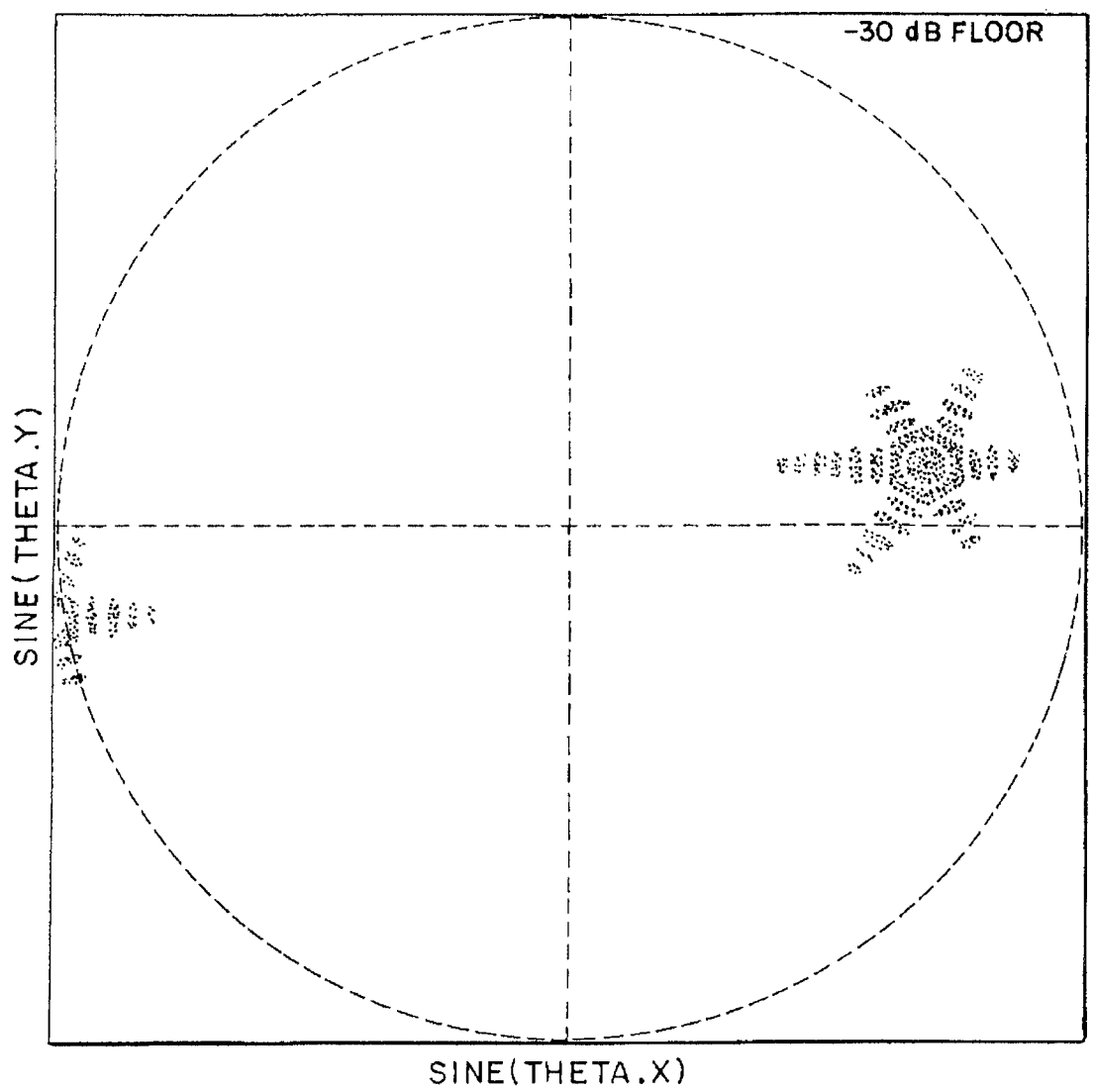

The macro elements 38 with irregular shape and/or acoustic elements 36 shifted in the acoustic layer 30 may reduce side lobes for a given scan line. FIG. 9A shows a three-dimensional field simulation of the main lobe and side lobes associated with a scan line using the periodic steps of the one-dimensional aperture of FIG. 8. At large steer angles, such as 45 degrees, the periodic jogs in the aperture created by wiring up $\lambda\backslash 2$ switch cells with $\lambda\backslash 2$ acoustic elements have the effect of concentrating acoustic energy in the field at specific angles away from the main lobe. The resulting side lobes may be quite severe at certain −rotational angles, exceeding −16 dB in some cases. FIG. 9B shows the same simulation, but for the one-dimensional aperture of FIG. 7. The side lobe in the acoustic field is eliminated or reduced, improving image contrast resolution.

Referring to FIGS. 2 and 5, the switch layer 34 has outputs. The outputs connect with or are switchably connectable with the ultrasound imaging system. The output is relative to the transducer probe 12, such as for receive operation, or relative to the imaging system, such as for transmit operation. The outputs extend through coaxial cables to a transducer connector. The transducer connector releasably connects with the imaging system. The imaging system, with the beamformer 14, uses the connections for scanning along a plane. Since the switch layer 34 configures the acoustic elements 36 into one-dimensional apertures, the beamformer 14 operates as if using a one-dimensional array. Fewer outputs are provided than a number of the acoustic elements, such as by at least half. Thousands of acoustic elements 36 may be provided, but are used to scan a volume with different one-dimensional apertures. This allows imaging systems with beamformer channels only sufficient for planar scanning to be used for volume scanning.

The outputs may include one or more bias signals. For example, bias voltage or voltages are provided for operation of a cMUT.

The outputs may include one or more signal lines for communications between the transducer probe 12 and the imaging system and/or for control signals. For example, an increment control signal is provided on one signal line. The increment signal, such as a pulse or transition, indicates that the next one-dimensional aperture is to be formed (e.g., rotation of the aperture).

The beamformer 14 is a transmit beamformer, receive beamformer, combinations thereof, or other now known or later developed device for scanning a region with the transducer probe 12. In one embodiment, the beamformer 14 includes transmitters or waveform generators for generating electrical waveforms for each element of a transmit aperture. The waveforms are associated with phase and amplitude. The waveforms for a given transmit event may have the same or different phasing. The electrical waveforms are relatively weighted and delayed to form an acoustic beam with a desired phase and amplitude characteristic. For example, the transmit beamformer includes amplifiers, phase rotators, and/or controllers to generate sequential, steered pulses with the desired phase and amplitude in relation to other acoustic beams. Converging, diverging or planar beams may be used.

The beamformer 14 may include receive beamformers, such as delays, phase rotators, amplifiers, and/or adders for relatively delaying and summing received signals to form one or more receive beams with dynamic focusing. For example, using shared processing, separate processing, or combinations thereof, a plurality (e.g., tens or hundreds) of parallel receive beamformers are provided to form a respective plurality of receive beams in response to a given transmit beam. Alternatively, the beamformer 14 includes a processor for Fourier or other analysis of received signals to generate samples representing different spatial locations of the scanned region.

The transducer probe 12 and beamformer 14 are connected together, such as the beamformer channels connecting through coaxial cables to the transducer probe 12. The transducer probe 12 and beamformer 14 are configured to scan a planar region or a segment of a planar region. The beamformer 14 is controlled or programmed to perform the scan. The beamformer parameters, such as relative delays and/or phasing for focus, apodization, beam amplitude, beam phase, frequency, or others, are set. The aperture for transmit and the aperture for receive on the transducer probe 12 is set. The beamformer 14 and transducer probe 12 are used to generate the waveforms for the aperture and convert the waveforms to acoustic energy for transmitting the beam, and used to receive acoustic energy at the receive aperture, convert the acoustic energy to electrical energy, and beamform the received electrical signals.

Electric steering may be used to scan a volume and/or plane. A volume scan may be performed using any pattern or distribution of scan lines and/or apertures. In one embodiment, an acquisition scan plane is positioned within a three-dimensional region by setting a one-dimensional aperture. Acoustic energy is transmitted in any of various now known or later developed scan patterns along the scan plane for acquiring data. The scan plane is then altered to another location in the volume by setting a different aperture.

For a given volume, the scans may be repeated. By repeating the scans, a sequence of frames of voxel data is obtained. Each frame represents the entire three-dimensional scanned volume, but may only represent smaller regions within the volume, such as a plane. By repeating the scanning, a plurality of frames of beamformed data representing the volume and/or plane within a given cycle is acquired. Any of scan line, part of frame, frame, or group of frame interleaving may be used.

The beamformer 14 may be configured, using the switches in the system, switches of the transducer probe 12, beamformer channel selection, combinations thereof, and/or other configuration approaches to interleave two or more moving apertures on the array. The configuration is performed using hardware, software, or combinations thereof. The two moving apertures move in different directions such that adjacent locations for the moving apertures are separated by five or fewer scans using other aperture locations of the moving apertures. For example, the moving apertures use two or four one-dimensional apertures. The different directions are counter rotation relative to the two-dimensional array for rotation. The beamformer 14 is configured to scan different planes for the different locations of the moving apertures. Alternatively, the different directions are counter translations, such as counter translation around a ring array where each aperture location is for scanning a different segment in a plane. Other rotation patterns for the scan planes may be used.

For each aperture position, the beamformer 14 is configured to scan with any scan line format. In one embodiment, the scan line density changes as a function of origin, angle, aperture location, or both. For example, less scan line density occurs along a plane for scan lines in the center. Different aperture locations may scan with different densities in different locations.

The interpolator 20 is part of the beamformer 14, the detector 18, or separate. The interpolator 20 is a memory, buffer, phase rotator, processor, adder, multipliers or other components for interpolating in-phase and quadrature or other signals with phase information. The interpolator 20 is configured as hardware, with software or combinations thereof to interpolate at least some of the data output by the beamformer 14. For example, one or more samples representing scan lines between received scan lines are interpolated. As another example, data for a scan line is replaced by interpolated data. The interpolated data is output to the detector 18. The detector 18 operates on interpolated data, actual received data, or combinations of both. In alternative embodiments, the interpolator 20 is not provided.

The detector 18 is configured to detect data output by the beamformer 14 and responsive to the moving apertures. The detector 18 is an ultrasound detector. The detector is configured by hardware and/or software to detect from the beamformed and/or interpolated data. Any detection may be used, such as B-mode, Doppler or color flow mode, harmonic mode, or other now known or later developed modes. B-mode and some harmonic modes use single pulse scan techniques for detection. The intensity of the received signals in the frequency band of interest is calculated. Multiple pulse techniques, such as flow mode estimation of velocity or energy, may be used.

The detector 18 detects the response to the transmit beams for the scan of the volume. The spatial and/or temporal resolution of the detected data is based on the beamforming or scanning resolution. Detected data representing the volume is provided. Such frames of data are provided for the same or similar volumes (e.g., similar accounts for unintended transducer and/or patient movement offsetting the volume) at different times throughout a heart cycle, over time, or merely once.

The processor 16 is a rendering processor configured by hardware and/or software. The processor 16 is a general processor, control processor, application-specific integrated circuit, field-programmable gate array, graphics processing unit, digital circuit, analog circuit, digital signal processor, combinations thereof, or other now known or later developed device for generating a three-dimensional rendering of a volume scanned with different planes. The processor 16 is a single device or group of devices. For example, the processor 16 includes separate processors operating in parallel or sequence. As another example, the processor 16 includes a network of devices for distributed processing in parallel or sequence. In one embodiment, the processor 16 is a specific device for three-dimensional image rendering, such as a graphics processing unit, graphics card, or other device for rendering.

The processor 16 uses surface rendering, projection rendering, alpha blending, texturing or other now known or later developed rendering. The data may be resampled to a regular voxel grid. Alternatively, the rendering is performed from data in a scan format, such as associated with the actual scan lines and/or interpolated scan lines. In yet other embodiments, the processor 16 is not provided or is a scan converter for generating a two-dimensional image representing a scanned plane or a reconstruction of a plane from a scanned volume.

The processor 16, the detector 18, or a separate processor generates images from the volume scan and/or plane scan or other data output from the detector 18. For example, grayscale and/or color coding is used to generate a B-mode, Doppler mode, or B-mode Doppler mode combination. Any image, such as a three-dimensional rendering, is output to the display 24.

The display 24 is a CRT, LCD, plasma, projector, printer, or other now known or later display device. The display 24 receives the image data from the processor 16 or other component and generates the image. A perfusion map, three-dimensional rendering, two-dimensional image, or other image is displayed. For example, a perfusion map is generated as a function of the detected contrast agents, such as modulating pixels by the perfusion rate for locations representing the tissue.

The memory 22 is a tangible computer readable storage medium, such as a cache, buffer, register, RAM, removable media, hard drive, optical storage device, or other computer readable storage media. The memory 22 is tangible by not being a signal, but a device. Computer readable storage media include various types of volatile and nonvolatile storage media. The memory 22 is part of the imager 17, the imaging system 16, or separate from both. The memory 22 is accessible by the processor 16.

In one embodiment, the memory 22 stores data for use by the processor 16, such as storing detected and/or image data. Additionally or alternatively, the memory 22 stores data representing instructions executable by the programmed processor 16 for scanning with ultrasound and/or controlling the switches of the transducer probe 12. The instructions for implementing the processes, methods and/or techniques discussed herein are provided on computer-readable storage media or memories. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

FIG. 10 shows a method for operating a two-dimensional transducer array in medical diagnostic ultrasound imaging. In one example embodiment, scanning of a three-dimensional volume is provided. In other embodiments, the scanning is of a plane. The method is implemented using the system of FIG. 1, the transducer probe 12 of FIG. 2, or a different system. The method is performed in the order shown or a different order. Additional, different, or fewer acts may be provided. For example, acts 42, 44, 46, 48, and/or 50 are not provided or provided in non-real time.

In act 37, a plurality of different apertures is formed in a multi-dimensional array of transducers. The apertures are formed by switching, such as one or more switches for each element connecting the elements together and/or to beamformer channels. For example, the switching and arrays described in U.S. Pat. No. 6,676,602, the disclosure of which is incorporated herein by reference, is used. As another example using the switching layer 34 and acoustic layer 30 discussed above, beamformer channels are connected to elements by two layers of switches, one layer having a channel matrix interconnected laterally and another layer having an acoustic element matrix interconnected to the channel matrix along another direction. Alternatively, one or more beamformer channels are turned on or off to include or not include a connected element in the aperture. Other aperture selections may be used.

Each aperture includes one or more transducers. For example, the apertures are one-dimensional. The aperture is formed from a plurality of transducers along a straight or curved line. In other embodiments, the apertures are multi-dimensional, such as having a 1.25D, 1.5D, or 1.75D arrangement of two or more rows of elements.

The switches or beamformer operation forming the aperture at a given time are configured to switch quickly, allowing real-time aperture change or operation free of mechanical movement. Electronic switching may occur more rapidly than mechanical movement. Any type of switch may be used for electronic movement of the aperture.

Each aperture is at a different position on an array. The aperture may slide along an array. For example, the aperture is translated laterally or in azimuth along an array of elements. As another example, the aperture rotates across the face of a multi-dimensional array. The rotation is about a center or other location on the multi-dimensional array, but may be about a point spaced from the face of the array. Each aperture is rotated by a different amount. In another example, the aperture translates laterally in elevation across a multi-dimensional array. Combinations of translation and rotation may be used. Each translated or rotated location corresponds to another aperture. The apertures in sequence correspond to a given aperture being translated or rotated to the different locations.

Any step size for the translation and/or rotation may be used. The step size is the same between each aperture location. For example, equal amounts of rotation are provided for each aperture location. In alternative embodiments, the step size for rotation and/or translation may vary, such as having a smaller step size to more heavily sample one region over another or to reduce frame rate by providing lesser sampling for some regions. Each of the different one-dimensional apertures corresponds to a different aperture rotation angle or position relative to the multidimensional array.

The transducers are in a hexagonal, rectangular, triangular, or other grid. Given the different positions of the one-dimensional apertures on the array, one or more of the apertures may have elements at a non-primary or non-natural angle to the grid, causing the elements to be other than along a straight line of the transducers. For example, a hexagonal grid has three primary axes along which a straight line of transducers may be connected. For other angles, the elements have jogs or steps to conform to the desired line.

For scanning, the different apertures correspond to different scan line positions. For example, the aperture is a one-dimensional aperture used to scan a plane. Scan lines in a sector, Vector™, linear or other format are used for scanning at the aperture location. The format is repeated at other aperture locations for other scan lines in the continuous region.

In act 39, the apertures of act 37 are formed by selecting transducers. The selected transducers (acoustic elements) are for forming a plurality of different elements of the one-dimensional array of the aperture. Substantially parallel groups of the transducers are selected for elements of the one-dimensional apertures. "Substantially" accounts for the shifts in the transducers and/or for aperiodic formation. The selected transducers in the groups are selected to be aperiodic along an elevation length of the corresponding elements. Any level of aperiodic may be provided, such as aperiodic in a range of frequencies at a bandwidth of operation of the array. Aperiodic elements have an irregular edge for each of the elements. The irregular edge is formed from connected adjacent transducers such that an azimuth width of the elements varies along the elevation length without periodic steps along the length of the element or at least half of the length of the element. For other elements, such as elements for angles along the primary direction of the grid, periodic distribution may be provided. The period of these elements has sufficiently high frequency to cause less side lobe at the imaging frequencies.

The aperiodic selection or shift in the frequency of periodicity may reduce the side lobes at the imaging frequency band. The side lobes for the one-dimensional apertures are reduced due to the groups being aperiodic as compared to selection of transducers in a periodic pattern along a line of the elements other than at the primary of the transducer grid.

The selection is performed with switches. The switches may have any arrangement. In one embodiment, the switches are grouped such that switch groups have a greater pitch than the transducers. The switch groups are sized to have an about one-half or less pitch of a center frequency of operation of the one-dimensional apertures. In one embodiment, the transducers are a first layer of microelectromechanical devices, and the switch groups are a second layer. The layers are stacked along a depth dimension. The switch groups include at least one switch configured to selectively connect with an adjacent switch group and at least two switches configured to selectively connect with respective transducers.

In additional or alternative embodiments, randomization or shifting of the transducers relative to each other is fixed or part of the layout (manufacture or design) of the transducer array. This introduces an irregular shape or pattern along the elements of the selected one-dimensional array.

In act 40, the one-dimensional apertures are connected with an ultrasound system for use as one-dimensional arrays. The connection is performed by switches, such as connecting beamformer channels through coaxial cables with entry switches adjacent to the array or aperture and spaced from the system. Separate channel connection (entry) switches are used, but other switches, such as edge switches or switches also used to interconnect elements, may be used. Another example connection is of the transducer assembly to the ultrasound system. This connection allows signal to pass between the imaging system and the transducer probe. The beamformer may be all in the imaging system, all in the transducer probe, or partially in the transducer probe and partially in the imaging system (partial beamformation in the probe).

In act 41, the connections of the channels with the array are controlled. The selection of the different one-dimensional apertures is controlled. The configuration of switches to form the aperture is loaded from the imaging system to the transducer probe. Alternatively, the configurations are preloaded in a programmable memory or a read only memory.

The connections may be controlled through indication of a specific aperture to use. In other embodiments, the connections are controlled by sequencing through a programmed or predetermined sequence of apertures. Based on an increment command, the next aperture in the sequence is selected. A signal on a single control line may indicate rotational or translation increment. A memory adjacent the multi-dimensional array and spaced from the ultrasound system controls the selecting in response to the rotational increment command provided by the ultrasound system.

Any sequence of apertures may be used. In one embodiment, an interleaved sequence of the different apertures is used for scanning. Two or more apertures are moved during the scanning. The aperture locations are grouped into two or more sets, each set providing the locations of apertures making up a given aperture movement. The scanning is interleaved between the sets, such as forming an aperture at one location for set 1, then forming an aperture at another location for set 2, then forming yet another location for set 1, and so on. Multiple apertures may be scanned from a given set before interleaving or switching to the apertures of another set. The order of the apertures within each set is arranged to reduce or minimize the amount of time between scanning adjacent portions of the scan region.

Figure 11:
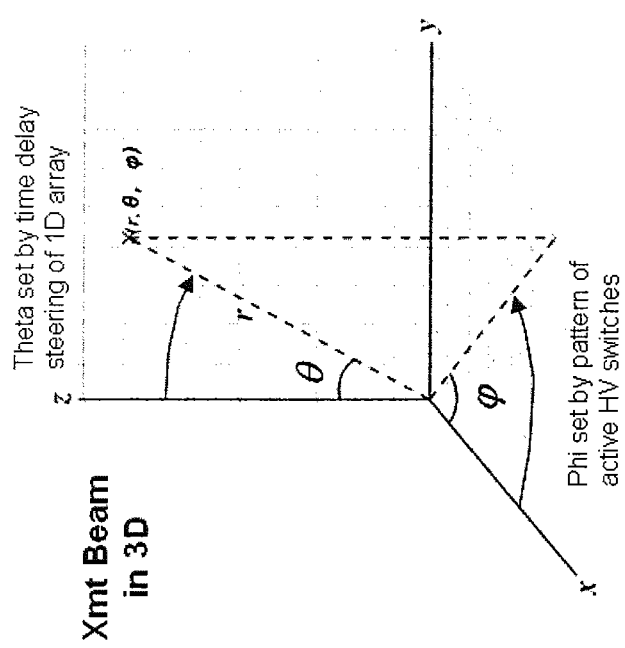
FIG. 11 is an example graphical illustration of aperture and scan line control to scan a volume.

In act 42, the apertures are used for scanning. One or more scan lines are formed for each aperture location or aperture. In the embodiment with a one-dimensional array for each aperture, a plurality (e.g., tens or hundreds) of scan lines are scanned. FIG. 11 shows scanning along a scan line selected by formation of the aperture and scan angle within the plane.

Figure 12:
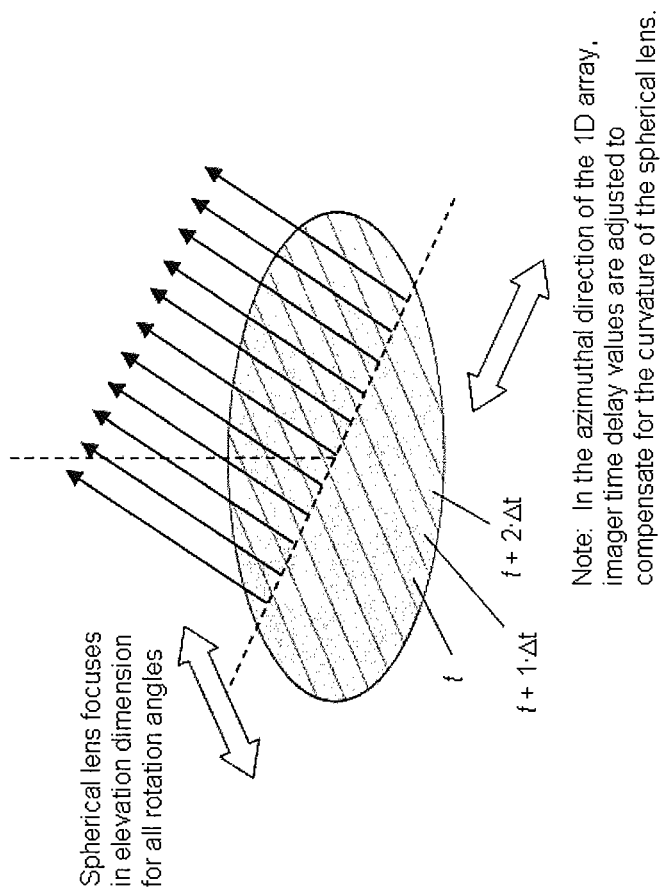
FIG. 12 is a graphical illustration of elevation focusing by a spherical lens.

Scanning is performed by beamformation. Relative delays and/or apodization determine the scan line origin and angle. For a one-dimensional array, the angle is an azimuth angle relative to the aperture. A spherical lens may provide elevation focus, as represented in FIG. 12

Acoustic energy is transmitted along the scan line. Receive beamformation samples the echoes from the transmitted acoustic energy along the same or a different scan line. In one embodiment, one scan line is used for each transmit and receive event. In another embodiment, the transmitted acoustic energy has a beam width in azimuth for receiving along two or more scan lines simultaneously or in response to the same transmitted beam. For example, eight receive beams are formed for each transmit beam. A fewer or larger number of receive beams may be formed for a given transmit event.

By scanning with a plurality apertures at different locations, a volume is scanned in one embodiment. A planar scan is provided in another embodiment, such as with the ring array. By scanning along a plurality of scan lines in a sequence, the continuous region may be sampled.

For the volume scan, the three-dimensional volume is scanned with ultrasound sequentially from the different one-dimensional or other apertures at different rotation angles and/or translations. In one embodiment, each aperture is used for scanning a plane. A two-dimensional beamformer may be used to sequentially scan a volume without the need for additional beamformer channels. For example, seven transmit events are performed for each plane or aperture. The transmit events have about 13 degree spacing to collect information for an about 90 degree sector or Vector™ scan for a given rotation angle slice. Multibeam receive samples the receive beam using 8-beams spaced about 1.6 degrees apart for each transmit beam. Combined, a scan of a planar slice uses 56 receive lines. Using sixty rotation angle slices or apertures spaced about 3 degrees apart, the contiguous volume region is scanned. The receive samples are combined into a data set or collected to sample the complete space over a full 180 degree rotation space. Sixty rotation angle slices by 7 transmit events requires 420 transmit events. If the depth to be sampled is about 150 mm, requiring about 200 μsec of round trip sound transit time, the volume sampling rate is about 12 Hz. This rate provides for visually acceptable real-time imaging while scanning. One example is given above. Different numbers of receive beams per transmit beam, number of transmit beams per plane or aperture, number of apertures, depths, or other values may be used.

The frame rate may be improved by reducing the lateral sampling density for angles near the center of the scan region as compared to the scan line density away from the center. The distribution of scan lines in the volume may be made more even, such that the density is similar at the center as at the edges of the volume. Other distributions may be provided by varying the scan line density azimuthally for each aperture location. The same variation in scan line density is used for each aperture location.

In act 44, data is received for the receive scan lines. The data is received by beamformation. Echoes impinging on the elements of the current aperture are transduced to electrical energy. The electrical energy from each element of the aperture is relatively delayed and/or weighted to beamform for a given location along each scan line. Digital and/or analog dynamic beamforming may be provided. The samples may be filtered or otherwise combined, such as for imaging at a cubic fundamental or phase inversion imaging. Any now known or later developed reception and formation of samples representing locations along one or more scan lines for each transmit event may be used.

By receiving data for each aperture, the planar or volume region is scanned. The data representing different locations within the region are provided.

In act 48, the received data and/or the interpolated data are detected. Any detection process may be used. For example, the intensity of the return is detected as B-mode data. As another example, the energy (power), velocity, and/or variance of moving tissue or fluid are detected as Doppler data. Contrast agent, harmonic, or other types of detection may be provided.

Some types of detection use a plurality of samples for each spatial location. The scanning of act 42 for a given aperture location is performed multiple times to acquire the data for the detection. The repetition is performed before scanning with a different aperture and/or for a different scan line. Alternatively, the sampling for detection may be interleaved with other scans.

In act 46, an image is generated from the detected data. The data received by scanning is used to generate the image. The image represents a volume, plane or line. For two-dimensional imaging, the data may be scan converted and mapped to display values. For example, B-mode information is mapped to a gray scale and Doppler data is mapped to a color scale.

For a volume, the image is rendered from the data representing the volume. Any now known or later developed rendering may be used. For example, surface rendering or projection rendering are performed. The image is rendered as a three-dimensional representation from data for the various scan planes. Alternatively, the data from the scan planes is interpolated to a regular grid, and the image is rendered from the grid data. Shading and/or opacity weighting may be used. The data may be filtered before or after image generation.

The generation of the image occurs in real-time with the scanning. For example, the image is generated while still scanning to acquire data for subsequent images. The image is generated in a same imaging session as the acquisition. The processing delay between scanning and generating the image may be a few seconds or less, such as less than one second. The volume is scanned a plurality of times each second. The images are generated at the scan rate in a short time to allow processing after completion of corresponding scans of the entire volume. In other embodiments, the data is stored. The image generation occurs from the stored data rather than being in real-time with the scanning.

While the invention has been described above by reference to various embodiments, it should be understood that many changes and modifications can be made without departing from the scope of the invention. The above embodiments are examples. It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A multi-dimensional transducer for medical diagnostic ultrasound imaging, the transducer comprising:
    a switching layer having a plurality of switch cells, each cell including at least one lateral switch for connecting to an adjacent cell and at least one vertical switch for connecting to an acoustic element; and
    an acoustic element layer having a plurality of the acoustic elements, the acoustic element layer stacked along a depth dimension with the switching layer, the acoustic elements comprising individual physical transduction devices separate from each other regardless of electrical connection;
    wherein the acoustic elements of the acoustic element layer and the corresponding individual physical transduction devices separate from each other regardless of electrical connection have a finer pitch in a direction orthogonal to the depth dimension than a pitch of the switch cells of the switch layer, resulting in a difference in physical pitch along the orthogonal direction within a face region of the acoustic elements,
    wherein a subset of the switches connect some of the acoustic elements to different beamformer channels, and
    wherein the difference in pitch provides for selection of most of the acoustic elements where some acoustic elements are deselected due to the difference in pitch of the switching layer and acoustic element layer in the stack along the depth dimension resulting in all of the switching cells being unavailable for the deselected some of the acoustic elements.

2. The multi-dimensional transducer of claim 1 wherein the switches are configured to form a one-dimensional array of one-dimensional array elements, at least one of the one-dimensional array elements comprising a plurality of the acoustic elements of the acoustic element layer connected together by the lateral switch.

3. The multi-dimensional transducer of claim 2 further comprising outputs configured to connect with an ultrasound imaging system, the outputs being fewer than a number of the acoustic elements by at least half.

4. The multi-dimensional transducer of claim 2 wherein the switches are configured to form additional one-dimensional arrays with the acoustic elements using different configurations of the lateral switches, the additional one-dimensional arrays rotated relative to the one-dimensional array on the acoustic element layer.

5. The multi-dimensional transducer of claim 1 wherein the switch cells have a regular hexagonal, rectangular, or triangular periodicity and wherein the acoustic elements have a different periodicity than the periodicity of the switch cells.

6. The multi-dimensional transducer of claim 1 wherein the acoustic elements are positioned aperiodically across a face of the transducer.

7. The multi-dimensional transducer of claim 6 wherein aperiodicity comprises shifts in the face by less than a pitch of the acoustic elements, different acoustic elements having different amounts and directions of shifts orthogonal to the depth dimension.

8. The multi-dimensional transducer of claim 6 wherein the switch cells each comprise three of the lateral switches and at least two of the vertical switches, the vertical switches operable to connect to different, but adjacent acoustic elements.

9. The multi-dimensional transducer of claim 1 wherein the vertical switches have a higher on resistance than the lateral switches.

10. The multi-dimensional transducer of claim 1 wherein the switching layer further comprises entry switches arranged along a geometric diagonal of the switch cells.

11. The multi-dimensional transducer of claim 1 further comprising a spherical lens positioned over the acoustic element layer.

12. A method for operating a two-dimensional transducer array in medical diagnostic ultrasound imaging, the method comprising:
 defining a plurality of different one-dimensional apertures on a multidimensional array of transducers, each of the different one-dimensional apertures corresponding to a different aperture rotation angle relative to the multidimensional array, the transducers comprising individual physical transduction devices separate from each other regardless of electrical connection; and
 selecting with switches substantially parallel groups of the transducers for elements of the one-dimensional apertures, the switches grouped such that switch groups have a greater pitch in a direction orthogonal to a depth dimension than a pitch of the transducers and the corresponding individual physical transduction devices separate from each other regardless of electrical connection, resulting in a difference in pitch between the transducers and the switches along the orthogonal direction within a face region of the acoustic elements, the selected transducers in the groups being aperiodic along an elevation length of the corresponding elements, a subset of the switches connecting the elements to different beamformer channels, and
 wherein the difference in pitch provides for selection of most of the transducers where some transducers are not connectable with switch cells due to the difference in pitch resulting in none of the switch cells being available for connection with the some of the transducers.

13. The method of claim 12 wherein aperiodic comprises having an irregular edge for each of the elements, the irregular edge formed from connected adjacent transducers such that an azimuth width of the elements varies along the elevation length without periodic steps.

14. The method of claim 12 wherein the switch groups are sized to have an about one-half pitch or less of a center frequency of operation of the one-dimensional apertures.

15. The method of claim 14 wherein the multidimensional array of transducers comprises a first layer of microelectromechanical devices and the switch groups comprises a second layer, the first and second layers stacked along the depth dimension, each of the switch groups including at least one switch configured to selectively connect with an adjacent switch group and at least two switches configured to selectively connect with respective transducers.

16. The method of claim 12 further comprising:
 connecting the one-dimensional apertures with an ultrasound system for use as one-dimensional arrays; controlling selection of the different one-dimensional apertures with a single control line, a signal on the single control line indicating rotational increment and a memory adjacent the multi-dimensional array and spaced from the ultrasound system controlling the selecting in response to the rotational increment.

17. The method of claim 12 wherein the transducers are in a hexagonal grid, one of the one-dimensional apertures has elements at an angle causing the elements to not be along a straight line of the transducers along any one of the three primary axes of the hexagonal grid; wherein side lobes for the one of the one-dimensional apertures are reduced due to the groups being aperiodic as compared to selection of transducers in a periodic pattern along a line of the elements.

18. A multi-dimensional transducer for medical diagnostic ultrasound imaging, the transducer comprising:
 a plurality of transducer elements, the elements comprising individual physical transduction devices separate from each other regardless of electrical connection;
 a plurality of switches grouped such that switch groups have a greater pitch in a direction orthogonal to a depth dimension than the transducer elements and corresponding individual physical transduction devices separate from each other regardless of electrical connection, resulting in a difference in pitch along the orthogonal direction within a face region of the acoustic elements, the switches configured to connect the transducer elements into a one-dimensional array of macro elements, the macro elements comprising groups of the transducer elements grouped such that different macro elements have edges that are not straight at different distances along an elevation length than others of the macro elements, including a subset of switches that connect the macro elements to different beamformer channels, and
 wherein some transducer elements are not connectable with the switches due the difference in pitch between the transducer elements and the switches resulting in none of the switch cells being available for connection with the some of the transducers.

19. The multi-dimensional transducer of claim 18 wherein the plurality of switches comprise a switching layer and are grouped in switch cells, each switch cell including at least one lateral switch for connecting to an adjacent switch cell and at least two vertical switches for connecting to respective transducer elements; and wherein the transducer elements comprise an element layer, each transducer element including at least one flexible membrane suspended over a gap for transducing between acoustic and electrical energies, the element layer stacked along the depth dimension with the switching layer; wherein the transducer elements of the element layer have a finer pitch than the pitch of the switch cells of the switch layer in the direction orthogonal to the depth dimension.

20. The multi-dimensional transducer of claim 18 wherein the switches are configured to form additional one-dimensional arrays with the transducer elements, the additional one-dimensional arrays rotated relative to each other and comprising macro elements.

21. The multi-dimensional transducer of claim 18 wherein the transducer elements are positioned aperiodically across a face of the transducer such that the transducer elements are shifted away from a periodic pattern by less than a pitch of the transducer elements in a direction orthogonal to the depth dimension, different transducer elements having different amounts and directions of shifts; and wherein the switches comprise vertical switches connectable with the transducer elements and lateral switches connectable with other lateral switches, the lateral switches having a lower on-resistance than the vertical switches.

* * * * *